United States Patent [19]
Benazzi et al.

[11] Patent Number: 6,130,363
[45] Date of Patent: *Oct. 10, 2000

[54] CATALYST WITH A BASE OF MODIFIED MFI ZEOLITE, AND ITS USE IN THE ISOMERIZATION OF A $C_8$ AROMATIC CUT

[75] Inventors: Eric Benazzi, Montesson; Jean-Francois Joly, Paris, both of France; Joao Miguel Da Silva, Mem Martins; Maria Filipa Gomes Ribeiro, Amadora, both of Portugal

[73] Assignee: Institut Francais du Petrole, Cedex, France

[*] Notice: This patent issued on a continued prosecution application filed under 37 CFR 1.53(d), and is subject to the twenty year patent term provisions of 35 U.S.C. 154(a)(2).

[21] Appl. No.: 08/890,703

[22] Filed: Jul. 11, 1997

Related U.S. Application Data

[60] Continuation of application No. 08/451,149, May 26, 1995, abandoned, which is a division of application No. 08/187,026, Jan. 27, 1994.

[30] Foreign Application Priority Data

Jan. 28, 1993 [FR] France .................................... 93 01016

[51] Int. Cl.[7] ...................................................... C07C 5/22
[52] U.S. Cl. ............................................ 585/481; 585/482
[58] Field of Search ............................ 208/138; 585/481, 585/482

[56] References Cited

U.S. PATENT DOCUMENTS

| | | |
|---|---|---|
| 3,702,886 | 11/1972 | Argauer et al. . |
| 4,427,790 | 1/1984 | Miale et al. ............................ 502/71 |
| 4,485,185 | 11/1984 | Onodera et al. ......................... 502/71 |
| 4,500,421 | 2/1985 | Chang et al. . |
| 4,654,316 | 3/1987 | Barri et al. . |
| 5,080,878 | 1/1992 | Bowes et al. . |
| 5,085,763 | 2/1992 | Dufresne et al. . |
| 5,242,676 | 9/1993 | Apelian et al. ......................... 423/714 |
| 5,281,566 | 1/1994 | Marcilly . |
| 5,338,525 | 8/1994 | Joly et al. . |

FOREIGN PATENT DOCUMENTS

| | | |
|---|---|---|
| 474536 | of 0000 | European Pat. Off. . |
| 082211 | 12/1981 | European Pat. Off. . |
| 0094288 | 4/1983 | European Pat. Off. . |
| 303527 | 8/1987 | European Pat. Off. . |
| 279568 | 2/1988 | European Pat. Off. . |
| 350367 | 6/1989 | European Pat. Off. . |
| 507656 | 3/1992 | European Pat. Off. . |
| 61-201618 | 9/1986 | Japan ...................................... 502/64 |

OTHER PUBLICATIONS

Translation of JP 61–201618.
Abstract of EP 303,527, Aug. 1987.
Abstract of JP 61–210618, Sep. 1986.
Abstract of EP 94,288, Apr. 1983.

*Primary Examiner*—Tom Dunn
*Attorney, Agent, or Firm*—Millen, White, Zelano & Branigan

[57] ABSTRACT

The invention is concerned with a catalyst comprising a matrix, a MFI type zeolite and at least one group VIII element, in which the crystals of the MFI type zeolite are desaluminated on their outer surface by at least one treatment with at least one solution of a fluorosilicate of a cation selected from the group formed by $NH_4^+$, alkylammoniums, $K^+$, $Na^+$, $Li^+$, $Ba^{2+}$, $Mg^{2+}$, $Cd^{2+}$, $Cu^+$, $Cu^{2+}$, $Ca^{2+}$, $Cs^+$, $Fe^{2+}$, $Co^{2+}$, $Pb^{2+}$, $Mn^{2+}$, $Rb^+$, $Ag^+$, $Sr^{2+}$, $Zn^{2+}$, $Tl^+$ and $H^+$, the global desalumination rate of said MFI zeolite thus treated being less than 5 atomic percent.

16 Claims, No Drawings

CATALYST WITH A BASE OF MODIFIED MFI ZEOLITE, AND ITS USE IN THE ISOMERIZATION OF A C₈ AROMATIC CUT

This appln is a continuation of Ser. No. 08/451,149, filed May 26, 1995, now abandoned, which is a divisional of application Ser. No. 08/187,026, filed Jan. 27, 1994.

BACKGROUND OF THE INVENTION

The present invention is concerned with an aluminosilicate type catalyst comprising an MFI zeolite, the selectivity and/or catalytic properties of which has/have been modified by desalumination of the outer surface of its crystals, and comprising at least one group VIII metal from the periodic classification of elements (Handbook of Chemistry and Physics, 65th edition, 1984–85), and a matrix. Said catalyst is used in isomerization reactions of $C_8$ aromatic hydrocarbons. The invention is also concerned with the process for the preparation of said catalyst. Usually, the outer surface of the zeolite crystals is modified by at least one treatment of the MFI by at least one solution of a fluorosilicic acid salt. Preferably, the salt selected does not result in the formation of aluminium salts which are not soluble in water.

At the present time, the catalysts used industrially in isomerisation reactions of $C_8$ aromatic cuts mainly have a base of ZSM-5 zeolite of MFI structural type, alone or mixed with other zeolites. These catalysts are described, in particular, in the patents U.S. Pat. No. 3,856,872, U.S. Pat. No. 4,098,836, U.S. Pat. No. 4,159,282, U.S. Pat. No. 4,467,129, U.S. Pat. No. 4,428,773, European Patent 138, 617 and U.S. Pat. No. 5,028,573.

The ZSM-5 zeolite is interesting because of its selectivity of shape which gives an advantageous selectivity with respect to para-xylene and also in its selectivity with respect to undesirable secondary dismutation reactions which remain at a lower level than those recorded on other zeolites with larger pore openings. In fact, 12MR zeolites with larger pore openings (opening with 12 oxygen atoms) have also been used, such as mordenite. The catalysts with a base of mordenite are described, in particular, in the patents U.S. Pat. No. 4,723,051, U.S. Pat. No. 4,665,258, and French Patent 2,477,903. However, these zeolites do not have special properties of geometric selectivity. This means that, irrespective of their Si/Al ratio, their selectivities with respect to para-xylene are lower than those obtained for ZSM-5 zeolite, and, in particular, there is a very great amount of trimethylbenzenes produced. The production of trimethylbenzenes by dismutation is actually promoted in mordenite whose microporous system is more open than that of ZSM-5: the openings are with 12 oxygens instead of 10 for ZSM-5.

SUMMARY OF THE INVENTION

The Applicant has surprisingly discovered that by carrying out at least one dealumination treatment of a MFI by using at least one fluorosilicic solution of a cation, and, in particular, at least one solution of ammonium hexafluorosilicate, it is possible to obtain active and selective catalysts for the isomerization reaction of $C_8$ aromatics. An overall or "global" dealumination rate is thus obtained which is less than 5% ion an atomic basis, i.e., for MFI zeolite thus treated, that is to say that the dealumination treatment draws off a maximum of 5% of the aluminium atoms present in the zeolite framework. The outer surface of the zeolite is dealuminated at least 37%, i.e., 37–61%, or 52–61%. Said treatment imparts to the MFI thus treated greatly improved selectivity properties. This is to be seen by a surprising inhibition of undesirable secondary reactions, such as the dismutation reaction, and by an increase in selectivity with respect to para-xylene. The new modified MFI also gives selectivities with respect to desalkylation reactions which are equivalent to those of catalysts with a base of untreated MFI. The solids thus obtained perform better than prior art MFI solids with isomerization of $C_8$ aromatics.

The MFI used in the catalyst of the present invention is prepared from a MFI which is synthesized just as well in hydroxide medium (U.S. Pat. No. 3,702,886) as in fluoride, in the presence of an organic structurer (for example, U.S. Pat. No. 5,010,048 and Patent Applications European Patent 342,075, European 469,151 and European Patent 472,462) or in the absence of an organic structurer (for example, European Application 500,413).

The MFI to which at least one treatment is given with at least one solution of fluorosilicic acid salts is preferably obtained directly on synthesis with the desired Si/Al atomic ratio, or is obtained by dealumination of a MFI which has a lower Si/Al ratio.

The MFI selectivity is modified by at least one treatment with at least one solution of fluorosilicate for MFI with a Si/Al atomic ratio which is between about 5 and 1000, preferably between 5 and 500, and still more preferably between 5 and 250. Said MFI are in the form of $Na^+$, $H^+$, $NH_4^+$, or they contain the organic structurer which was used in their synthesis, or they are all in the form of mixed combinations of the four forms cited hereinabove, preferably in the form of $NH_4^+$ and/or the form containing the organic structurer.

When the treatment with at least one fluorosilicate solution is carried out on $NH4^+$ forms of MFI, the following methods are used for placement in $NH_4^+$ form, depending on the case at hand:

a) The MFI has been synthesized in the absence of organic structurer. In this case, the crude MFI from the synthesis operation contains sodium in its microporosity which is removed by several ionic exchanges with concentrated solutions of ammonium nitrate (10N) which allows a content of sodium by weight to be obtained in relation to weight of dry MFI which is usually less than 2000 ppm, preferably less than 1000 ppm, and, more preferably still, less than 500 ppm.

b) The MFI has been synthesised in the presence of an organic structurer. In this case the crude MFI from the synthesis operation contains the organic structurer and sodium in its microporosity. The crude MFI from the synthesis operation is first of all subjected to a calcination operation in air in order to remove from its structure practically all the organic structurer which is found there. Then, it is subjected to a plurality of ionic exchanges by concentrated solutions of ammonium nitrate (10N) which enable a content by weight of sodium to be obtained in relation to the weight of dry MFI which is usually less than 2000 ppm, preferably less than 1000 ppm, and still more preferably less than 500 ppm.

When the treatment with at least one fluorosilicate solution is carried out directly on the MFI forms containing the organic structurer no initial treatment is carried out on the MFI. The residual sodium contained in the microporosity of the zeolite is thus practically eliminated, after said treatment, by carrying out three ionic exchanges with solutions of ammonium nitrate.

The fluorosilicate used as the dealumination agent and as the silicon source which enable silicon atoms to be reinserted into the crystal network of the MFI to replace the aluminium atoms removed can be one of the salts of the following formula: $M_{2/x}SiF_6$ where M is a metal cation or non-metallic cation with the valence x. The M cations can thus be $NH_4^+$, an alkylammonium, $K^+$, $Na^+$, $Li^+$, $Ba^{2+}$, $Mg^{2+}$, $Cd^{2+}$, $Cu^+$, $Cu^{2+}$, $Ca^{2+}$, $Cs^+$, $Fe^{2+}$, $Co^{2+}$, $Pb^{2+}$, $Mn^{2+}$, $Rb^+$, $Ag^+$, $Sr^{2+}$, $Zn^{2+}$, $Tl^+$ and $H^+$. Preferably, ammonium hexafluorosilicate is used because it results in the formation of aluminium salt $(NH_4)_3AlF_6$ which is soluble in water which can be easily eliminated. Usually, the treatment temperature is between 20 and 100° C., and preferably between 50 and 100° C. The treatment of the MFI is carried out in the presence of ammonium acetate which enables the pH of the reaction medium to be fixed at values of between 4 and 8, preferably between 5.5 and 7, these being pH values for which the zeolite does not suffer any destruction to the framework by direct acid attack.

After the step where fluorosilicate solution is added to the MFI suspension in an ammonium acetate solution, the reaction mixture is left, with vigorous agitation, at the desired temperature for a period of between 30 minutes and 48 hours, but preferably between 1 and 5 hours.

The MFI is then filtered at the reaction temperature and is washed thoroughly in boiling water. The volume of boiling water used for these washing operations corresponds to a v/p=150 ml/g, (the v/p ratio is the ratio of the volume of boiling water to the amount of dry zeolite treated. The MFI type zeolite is dried in a flow of air at 450° C. for 4 hours).

After this (these) treatment(s), the modified MFI is subjected to a heat treatment which is intended either to decompose the ammonium cations present within the network and to thus obtain the acid form (H-M) of the MFI if the treatment has been carried out on the $NH_4^+$ form of the MFI, or it is subjected to a calcination operation in air to remove the organic structurer, followed by a plurality of ionic exchanges with concentrated solutions of ammonium nitrate (10N) which enable a content by weight of sodium to be obtained in relation to the dry MFI which is usually less than 2000 ppm, preferably less than 1000 ppm, and, still more preferably, less than 500 ppm in instances where the treatment is carried out on the MFI containing the organic structurer which has been used for its synthesis.

The zeolite can then be subjected to the deposit of at least one group VIII metal, preferably selected from the group formed by platinum and palladium, and shaped using any technique known to the skilled person. It can, in particular, be mixed with a matrix, usually amorphous, for example with a damp powder of alumina gel. The mixture is then shaped, by extrusion, for example, through a drawplate. The content of MFI in the mixture thus obtained is usually between 0.5 and 99.99% and advantageously between 40 and 90% by weight in relation to the mixture (MFI+matrix). It is more particularly between about 10 and 60%, and, preferably, between about 15 and 40% by weight in relation to the mixture (MFI+matrix).

In that which follows, the term, "support" will be used to denote the mixture of MFI+matrix.

The shaping operation can be carried out with matrices other than alumina, such as magnesium, silica alumina, natural clays (kaolin, bentonite) and by way of other techniques than extrusion techniques, such as the formation of pastilles or dragées.

The hydrogenizing group VIII metal, preferably Pt and/or Pd, can also be deposited on the support using any process known to the skilled person enabling the metal to be deposited on the MFI. It is possible to use the cationic exchange technique competitively where the competitor is preferably ammonium nitrate, the competition ratio being at least equal to about 50 and advantageously about 50 to 200. With platinum or palladium, a tetramine complex is usually used of platinum, or a tetramine complex of palladium: these latter are then practically all deposited over the MFI. This cationic exchange technique can also be used for directly depositing the metal on the MFI powder, before it is eventually mixed with a matrix.

Depositing of the group VIII metal (or metals) is usually followed by a calcination operation in air or oxygen, usually between 300 and 600° C. for 0.5 to 10 hours, preferably between 350° C. and 550° C. for 1 to 4 hours. Reduction is then possible in hydrogen, usually at a temperature of between 300 and 600° C. for 1 to 10 hours; preferably, the operation takes place between 350° C. and 550° C. for 2 to 5 hours. The content of group VIII metal (preferably Pt and/or Pd) deposited on the catalyst which is obtained after the end of the exchange operation is usually between 0.05 and 1.5%, preferably between 0.1 and 1% by weight in relation to the catalyst as a whole.

It is also possible to deposit platinum and/or palladium no longer directly on the MFI, but on the aluminic binding agent, before or after the shaping operation, by carrying out anionic exchange with hexachloroplatinic acid, hexachloropalladic acid and/or palladium chloride in the presence of a competitor agent, for example hydrochloric acid. Usually, after platinum and/or palladium has/have been deposited, the catalyst is subjected to a calcination operation, as before, and then reduced in hydrogen, as stated hereinabove.

The bifunctional catalyst obtained by way of the above operations can be used particularly in isomerization reactions for an aromatic $C_8$ cut comprising either a mixture of xylenes alone or a mixture of xylene(s) and ethylbenzene. The isomerization of alkyl-aromatics, and, in particular, of xylenes, is very important commercially. Usually, it is para-xylene, in particular, which is the most sought after product because it is used, in particular, as an intermediate item in the manufacture of polyester fibres. It is preferable to manufacture para-xylene by isomerising meta-xylene, this latter being obtainable by isomerisation of ortho-xylene. Since it is difficult to separate ethyl benzene by distillation of the mixture of xylenes (the boiling points of the various compounds are very close), ethyl benzene is very often found in the isomerisation charge of aromatic $C_8$ hydrocarbons.

The operating conditions of the isomerization process for an aromatic $C_8$ cut which is carried out in the presence of at least one catalyst according to the invention are as follows:

temperature between 240 and 600° C., preferably between 350 and 510° C., pressure between 0.05 and 10 MPa, preferably between 0.2 and 3 MPa, spatial speed (pph, in mass of charge per unit of charge of catalyst and per hour), between 0.5 and 200 $h^{-1}$, preferably between 2 and 100 $h^{-1}$, molar ratio of hydrogen to hydrocarbon of the charge ($H_2$/HC) between 0.5 and 12, preferably between 2 and 6.

The following examples illustrate the invention, without, however, limiting its scope; they are given either for a charge which is formed of 80% ortho-xylene and of 20% ethylbenzene (% by weight), examples 2, 3, 5 and 6, or for a charge which is formed of 80% meta-xylene and 20% ethyl benzene (% by weight), examples 1 and 4.

EXAMPLES

Example 1

Catalyst C1 According to the Invention

The raw material used is an MFI which is synthesized in a fluoride medium which has a global atomic Si/Al ratio of 10.5 and a content by weight of sodium in relation to dry MF1 of about 7%.

The MFI is first of all subjected to 3 ionic exchanges in a solution of 10N NH$_4$NO$_3$ at about 100° C. for 4 hours for each exchange. The content by weight of sodium is thus less than 50 ppm. The MFI form NH$_4^+$ then has a global Si/Al ratio of 10.5, a Si/Al ratio measured by XPS (ESCA) characteristic of the outer surface of the MFI crystallites of 10, an elementary mesh volume of 5.393 nm$^3$, a porous volume in nitrogen, measured at −196° C. and with P/Po= 0.19 of 0.22 cm$^3$ of liquid per gram of MFI and a specific surface measured using the B.E.T. method of 410 m$^2$/g.

The MFI form NH$_4$ obtained hereinabove is then subjected to treatment with a solution of ammonium hexafluorosilicate. To that end, 20 grams of dry zeolite is placed in suspension in 400 ml of a solution of ammonium acetate (30 grams of ammonium acetate for 200 ml distilled water). This suspension is then placed in a 500 ml tricol provided with a reflux, and mechanical agitation means. The initial pH of the medium is 7.05. The temperature is brought to 80° C. Then, using a pump, 116 ml of a solution of 0.5 M ammonium hexafluorosilicate is introduced. After adding it the amount of ammonium hexafluorosilicate injected is 0.29 mole for 100 grams dry zeolite. The system is kept at the reaction temperature for another 2 hours. Then, the solution is cooled to ambient temperature, and the measured value of the pH at the end of the reaction is 6.1. The solid is then filtered and washed with at least 6 liters of boiling distilled water, that is to say with at least 300 ml distilled water per gram of dry zeolite (V/P=300 ml/g). The zeolite thus treated is dried in the test tube at 105° C. for one night, and then calcined in air in such a way as to remove the ammonia from the MFI and to obtain the H$^+$ form. The solid obtained after these treatments is called HMFI-1.

This latter is then thoroughly mixed with the alumina on which 0.3% by weight of platinum is dispersed. The catalyst formed by the HMFI-1 mixture plus alumina contains 40% by weight of alumina. The content by weight of the platinum of the end catalyst (containing HMFI-1) is thus about 0.12% by weight.

The C1 catalyst thus produced is then shaped by a pastille-forming operation, calcined in air at 550° C. for 2 hours and reduced in hydrogen to 500° C. for 3 hours.

The catalyst C1 is then tested with isomerization of the meta-xylene mixture (80% by weight) and ethyl benzene (20% by weight) at a temperature of 410° C., at a pressure of 1.2 MPa and with a molar ratio of hydrogen to hydrocarbons (H$_2$/HC) of about 4.

The performance of the catalyst C1 and of the catalysts prepared in the following examples, given in Table 1, are defined by:

$$\text{Conversion of o-xylene (\%)} = \frac{\text{mass of o-xylene in the charge} - \text{mass of o-xylene in the product}}{\text{mass of o-xylene in the charge}} \times 100$$

Conversion of meta-xylene (%)=\F(mass of meta-xylene in the charge−mass of meta-xylene in the product; mass of meta-xylene in the charge)×100

Selectivity with respect to isomerisation (%) =

$$\frac{\text{mass of m-xylene} + \text{mass of p-xylene}}{\text{mass of products}} \times 100$$

Approach to equilibrium of o-xylene (AEQ-ox) (%) =

$$\frac{\text{number of moles of o-xylene in the product}}{\text{number of moles of o-xylene at thermodynamic equilibrium}} \times 100$$

Approach to equilibrium of the meta-xylene (AEQ-mx) =

$$\frac{\text{number of moles of the meta-xylene in the product}}{\text{number of moles of the meta-xylene at thermodynamic equilibrium}} \times 100$$

Yield of C$_8$ aromatic (%) =

$$\frac{\text{mass of C}_8 \text{ aromatics and naphthenes in the product}}{\text{total mass of C}_8 \text{ aromatics in the charge}} \times 100$$

Selectivity with respect to dismutation (%) =

$$\frac{\text{mass of trimethylbenzene} + \text{mass of benzene}}{\text{mass of products}} \times 100$$

Selectivity with respect to dismutation (%) =

$$\frac{\text{mass of trimethylbenzenes} + \text{mass of toluene} + \text{mass of benzene}}{\text{mass of benzene}} \times 100$$

Selectivity with respect to cracking (%) = $\frac{\text{mass of C}_1 \text{ to C}_4 \text{ gases}}{\text{mass of products}} \times 100$ Example 2

Catalyst C2 According to the Invention

The raw material used is an MFI in H$^+$ form which has a Si/Al atomic ratio of 27, an elementary mesh volume of 5.341 nm$^3$, a content of sodium of less than 50 ppm by weight, a porous volume in nitrogen, measured at −196° C. and with P/Po=0.19 of 0.19 cm$^3$ of liquid per gram of MFI and a specific surface measured using the B.E.T. method of 439 m$^2$/g.

The MFI is first of all subjected to 3 ionic exchanges in a solution of 10N NH$_4$NO$_3$ at about 100° C. for 4 hours, for each exchange, in such a way as to obtain it in NH$_4^+$ form. It thus has a Si/Al ratio measured by XPS (ESCA) which is characteristic of the outer surface of the MFI crystallites of 26, almost identical to the global Si/Al ratio measured by X fluorescence (FX).

The MPI form NH$_4^+$ obtained hereinabove is then subjected to the treatment with ammonium hexafluorosilicate. To that end, 20 grams of dry zeolite is placed in suspension in 200 ml of a solution of ammonium acetate (20 grams of ammonium acetate for 200 ml distilled water). This suspension is then placed in a 500 ml tricol which is provided with a reflux, and with mechanical agitation means. The initial pH of the medium is 7.0. The temperature is brought to 80° C. Then, with the aid of a pump, 80 ml of a 0.3 M ammonium hexafluorosilicate solution is introduced. After it has been added, the amount of ammonium hexafluorosilicate injected represents 0.12 moles for 100 grams of dry zeolite. The system is kept at the reaction temperature for another 2 hours. Then, the solution is cooled to ambient temperature, and the measured pH value at the end of the reaction is 5.5. The solid is then filtered and washed with at least 6 liters of boiling distilled water, that is to say at least 300 ml distilled water per gram of dry zeolite (V/P=300 ml/g). The zeolite thus treated is dried in the test tube at 105° C. for one night, then calcined in dry air in such a way as to remove the ammonia from the MPI and to obtain the $H^+$ form. The solid obtained at the end of these treatments is called HMFI-2.

The characteristics of the solid obtained (catalyst C2) are a global atomic Si/Al ratio of 27 and a Si/Al ratio of the XPS surface of 403. The surface ratio is measured by XPS (ESCA) and is characteristic of the outer surface of the crystals of the MFI treated.

The steps for mixing the MFI and the alumina, for dispersing the platinum, for shaping, reducing the catalyst and the catalysts and the conditions for the isomerization test are identical to those described in Example 1.

The catalyst C2 is then tested with respect to isomerization of the mixture of ortho-xylene (80% by weight) and ethylbenzene (20% by weight), at a temperature of 410° C., at a pressure of 1.2 MPa and with a molar ratio of hydrogen to hydrocarbons ($H_2$/HC) of about 4.

The performances of the catalyst C2 thus obtained and according to the invention (whose platinum content is about 0.12% by weight) are shown in Table 2.

Example 3

Catalyst C3 According to the Invention

The raw material used is a MFI containing the organic structurer which has been used for its synthesis and which has an atomic Si/Al ratio of 45 (measured by X fluorescence) and an elementary mesh volume of 5.367 $nm^3$, a sodium content of 0.7% by weight.

The MFI described hereinabove is subjected to the treatment with ammonium hexafluorosilicate. To that end, 20 grams of dry zeolite is placed in suspension in 200 ml of a solution of ammonium acetate (20 grams of ammonium acetate for 200 ml distilled water). This suspension is then placed in a 500 ml tricol which is provided with a reflux, and with mechanical agitation means. The initial pH of the medium is 6.8. The temperature is brought to 80° C. Then, with the aid of a pump, 55 ml of a solution of 0.4 M ammonium hexafluorosilicate is introduced. After it has been added, the amount of ammonium hexafluorosilicate injected is 0.11 mole for 100 grams dry zeolite. The system is kept at the reaction temperature for another 2 hours. Then, the solution is cooled to ambient temperature, and the measured pH value at the end of the reaction is 5.7. The solid is then filtered and washed with at least 6 liters of boiling distilled water, that is to say at least 300 ml distilled water per gram of dry zeolite (V/P=300 ml/g). The zeolite thus treated is dried in the test tube at 105° C. for one night, and then it is calcined in dry air in such a way as to completely remove the organic structurer contained in its pore structure. Then, the MFI is subjected to 3 ionic exchanges in a solution of 10N $NH_4NO_3$ at about 100° C. for 4 hours, for each exchange, in order to obtain it in the $NH_4^+$ form. Finally, the MFI treated and in $NH_4^+$ is calcined in dry air in order to remove the ammonia from it and to obtain the $H^+$ form. The solid obtained after these treatments is called HMFI-3.

The steps for mixing the MFI and the alumina, for dispersing the platinum, for shaping and for reducing the catalyst are identical to those described in Example 1.

The characteristics of the solid obtained (catalyst C3) are a global atomic Si/Al ratio of 45 and a Si/Al XPS surface ratio above 95. The surface ratio is measured by XPS (ESCA) and is characteristic of the outer surface of the crystals of the MFI treated.

The catalyst C3 is then tested with respect to isomerization of the mixture of ortho-xylene (80% by weight) and ethylbenzene (20% by weight) at a temperature of 410° C., at a pressure of 1.2 MPa and with a molar ratio of hydrogen to hydrocarbons ($H_2$/HC) of about 4.

The performance of the catalyst C3 thus obtained and according to the invention (whose platinum content is about 0.12%) are given in Table 2.

Example 4

NC1 Catalyst Not According to the Invention

The raw material used in this example is MFI in $NH_4^+$ form, prepared in Example 1, but not treated according to the invention.

This latter is then thoroughly mixed with the alumina on which 0.3% by weight of platinum is dispersed. The catalyst constituted of the mixture MFI+alumina contains 40% by weight of alumina. The content by weight of platinum of the end catalyst (containing MFI) is thus about 0.12% by weight.

The NC1 catalyst thus produced is then shaped by a pastille forming operation, calcined in air at 550° C. for 2 hours and reduced in hydrogen at 500° C. for 3 hours.

The NC1 catalyst is then tested with isomerization of the mixture of meta-xylene (80% by weight) and ethylbenzene (20% by weight), at a temperature of 410° C., at a pressure of 1.2 MPa and with a molar ratio of hydrogen to hydrocarbons ($H_2$/HC) of about 4.

The performance of the NC1 catalyst are given in Table 1.

Example 5

Catalyst NC2 Not According to the Invention

The raw material used in this example is the MFI in $H^+$ form used in Example 2 and not treated according to the invention.

The steps for forming $NH_4^+$ from the MFI, for mixing the MFI and the alumina, for dispersing the platinum, for shaping and reducing the catalyst are identical to those described in Example 1.

The catalyst NC2 is then tested with respect to isomerization of the mixture of ortho-xylene (80% by weight) and ethyl benzene (20% by weight) at a temperature of 410° C., at a pressure of 1.2 MPa and with a molar ratio of hydrogen to hydrocarbons ($H_2$/HC) of about 4.

The performance of the catalyst NC2 thus obtained and not according to the invention (whose platinum content is about 0.12%) are given in Table 2.

Example 6

Catalyst NC3 Not According to the Invention

The raw material used in this example not according to the invention is a MFI containing the organic structurer which has been used for its synthesis and which has an atomic Si/Al ratio of 45, but which is not treated according to the invention.

The zeolite is dried in the test tube at 105° C. for one night, then calcined in dry air in order to completely remove the organic structurer contained in its pore structure. The MFI is then subjected to 3 ionic exchanges in a solution of 10N $NH_4NO_3$ at about 100° C. for 4 hours, for each exchange operation in such a way as to obtain it in $NH_4^+$ form. Finally, the MFI treated and in $NH_4^+$ form is calcined in dry air in order to remove the ammonia from it and to obtain the $H^+$ form.

The steps for mixing the MFI and the alumina, for dispersing the platinum, for shaping and for reducing the catalyst are identical to those described in Example 1.

The catalyst NC3 is then tested with respect to isomerization of the mixture of ortho-xylene (80% by weight) and ethylbenzene (20% by weight) at a temperature of 410° C., at a pressure of 1.2 MPa and with a molar ratio of hydrogen to hydrocarbons ($H_2$/HC) of about 4.

The performance of the catalyst NC3 thus obtained and not according to the invention (whose platinum content is about 0.12% by weight) are given in Table 2.

Effect of Treatments of MFI by Ammonium Hexafluorosilicate, on Selectivities at Iso-Approach to Equilibrium Table 1 describes the performance of the catalysts C1 and NC1 and Table 2 describes that of the catalysts C2, C3, NC2 and NC3, prepared according to the modes of operation described hereinabove. The effect of the treatment with ammonium hexafluorosilicate on selectivities is particularly apparent.

TABLE 1

| Charges | 80% (by weight) meta-xylene + 20% (by weight) ethylbenzene | |
| --- | --- | --- |
| Catalysts | NC1 | C1 |
| Examples | 4 | 1 |
| % AEQ meta-xylene | 95 | 95 |
| % yield $C_8$ (aromatics + naphthenes) | 68 | 82 |
| % Dismutation | 17 | 8 |
| % Desalkylation | 16 | 14 |
| % Cracking | 7 | 3 |
| Ratio of para-xylene/meta-xylene | 0.43 | 0.65 |

TABLE 2

| Charges | 80% (by weight) ortho-xylene + 20% (by weight) ethylbenzene | | | |
| --- | --- | --- | --- | --- |
| Catalysts | NC2 | C2 | NC3 | C3 |
| Examples | 5 | 2 | 6 | 3 |
| % AEQ o-xylene | 97 | 97 | 96.5 | 96.5 |
| % Yield $C_8$ (aromatics + naphthenes) | 67 | 80 | 70 | 79 |
| % Dismutation | 14 | 6 | 16 | 9 |
| % Desalkylation | 13 | 12 | 12 | 11 |
| % Cracking | 4.5 | 1.5 | 2 | 1 |

In Tables 1 and 2, the values for the spatial speeds (pph) in (hours)-1 adjusted to obtain % AEQ of ortho-xylene and meta-xylene are comparable.

The catalyst C1 according to the invention exhibit higher performance than the prior art NC1 catalyst NC1. In fact, at iso-approach to equilibrium of the meta-xylene, the rate of secondary dismutation reactions which leads, i.a., to the formation of trimethylbenzenes is greatly reduced in instances where the catalyst is the catalyst C1 according to the invention. On the other hand, it appears that the catalyst treated according to the invention (C1) gives a cracking rate which is lower than the prior art catalyst NC1, but gives, in particular, greater selectivity with respect to para-xylene isomer. As a result, the yield of $C_8$ aromatics+naphthenes obtained with the catalyst is greater than that of the prior art catalyst. The catalyst treated according to the invention thus has the two-fold advantage that the rate of undesirable reactions is reduced (dismutation and cracking reactions), while the selectivity with respect to para-xylene formed is increased.

The catalysts C2 and C3 according to the invention show higher performance than the catalysts NC2 and NC3 of the prior art. In fact, at iso-approach to equilibrium of the o-xylene, the isomerization yield of $C_8$ aromatics+ naphthenes obtained on the catalysts C2 and C3 is greater than that of the catalysts NC2 and NC3. On the other hand, with the MFI treated according to the invention (catalysts C2, C3), the secondary dismutation reaction which results in the formation of trimethylbenzenes is greatly inhibited in comparison to that obtained in the presence of non selective MFI (catalysts C2 and C3). Likewise, the rate of the cracking reactions is greatly reduced on catalysts containing MFI zeolite which has been subjected to the treatment with at least one aqueous solution of ammonium hexafluorosilicate according to the invention. Moreover, it can be seen that the rate of the desalkylation reactions is not modified by the treatment carried out according to the invention.

The X fluorescence analysis on the MFI; HMFI-1, HMFI-2 and HMFI-3 treated according to the invention shows that the global (atomic) Si/Al ratios thus measured are substantially identical to the global (atomic) Si/Al ratios of the initial MFI prior to treatment. On the other hand, an increase in the Si/Al ratios measured by XPS (ESCA) is noted after the treatment according to the invention.

What is claimed is:

1. A process for the isomerization of a $C_8$-aromatic cut, comprising subjecting said cut to effective conditions in the presence of a catalyst comprising a matrix, an MFI zeolite and at least one group VIII element, wherein crystals of the MFI zeolite are dealuminated on outer surfaces at least 37% by at least one treatment with at least one solution of a fluorosilicate having a cation which is $NH_4^+$, an alkylammonium, $K^+$, $Na^+$, $Li^+$, $Ba^{2+}$, $Mg^{2+}$, $Cd^{2+}$, $Cu^+$, $Cu^{2+}$, $Ca^{2+}$, $Cs^+$, $Fe^{2+}$, $Co^{2+}$, $Pb^{2+}$, $Mn^{2+}$, $Rb^+$, $Ag^+$, $Sr^{2+}$, $Zn^{2+}$, $Tl^+$, or $H^+$, the overall dealumination of said zeolite thus treated being less than 5 percent on an atomic basis, the atomic Si/Al ratio of the MFI zeolite prior to treatment with fluorosilicate being at least 5 and less than 100.

2. A process according to claim 1, wherein the MFI zeolite is treated with a an ammonium hexafluorosilicate solution.

3. A process according claim 1, wherein the treatment is carried out between 20 and 100° C. and at a pH of between 4 and 8.

4. A process according claim 1, wherein the group VIII element is platinum or palladium.

5. A process according claim 1, wherein the group VIII element is deposited on the zeolite.

6. A process according claim 1, wherein the group VIII element is deposited on the matrix.

7. A process according to claim 1, wherein the matrix is alumina, magnesium, silica alumina, natural clays, or a mixture thereof.

8. A process according to claim 1, conducted at a temperature between 240 and 600° C., a pressure is between 0.05 and 10 MPa, a spatial speed is between 0.5 and 200 h$^{-1}$, and a H$_2$/HC molar ratio between 0.5 and 12.

9. A process according to claim 8, in which the cut treated is a mixture of xylene.

10. A process according to claim 9, in which the cut treated also contains ethyl benzene.

11. A process according to claim 1, wherein the catalyst is dealuminated on its outer surface at least 37–61%.

12. A process according to claim 1, wherein the catalyst is dealuminated on its outer surface at least 52–61%.

13. A process for the isomerization of a C$_8$-aromatic cut, comprising subjecting said cut to isomerization conditions in the presence of a catalyst comprising a matrix, a MFI zeolite and at least one group VIII element, wherein the MFI zeolite is dealuminated on its outer surface at least 37% on an atomic basis and dealuminated overall less than 5% on an atomic basis, said dealumination being effected by at least one treatment with at least one solution of a fluorosilicate having a cation which is NH$_4^+$, an alkylammonium, K$^+$, Na$^+$, Li$^+$, Ba$^{2+}$, Mg$^{2+}$, Cd$^{2+}$, Cu$^+$, Cu$^{2+}$, Ca$^{2+}$, Cs$^+$, Fe$^{2+}$, Co$^{2+}$, Pb$^{2+}$, Mn$^{2+}$, Rb$^+$, Ag$^+$, Sr$^{2+}$, Zn$^{2+}$, Tl$^+$, or H$^+$.

14. A catalyst according to claim 13, in which the MFI zeolite prior to dealumination has an atomic Si/Al ratio of between 5- less than 100.

15. A process according to claim 13, wherein the catalyst is dealuminated on its outer surface at least 37–61%.

16. A process according to claim 13, wherein the catalyst is dealuminated on its outer surface at least 52–61%.

\* \* \* \* \*